United States Patent [19]

Enomoto et al.

[11] Patent Number: 4,487,770

[45] Date of Patent: Dec. 11, 1984

[54] TREATMENT OF DISEASES OF THE LIVER, KIDNEY, COLON AND RECTUM

[75] Inventors: Hiroshi Enomoto, Nagaokakyo; Akira Nomura, Hirakata; Yoshiaki Aoyagi, Otsu; Fusao Ueda, Shiga, all of Japan

[73] Assignee: Nippon Shinyaku Co., Ltd., Japan

[21] Appl. No.: 411,593

[22] Filed: Aug. 26, 1982

[30] Foreign Application Priority Data

Sep. 25, 1981 [JP] Japan .................................. 56-152471

[51] Int. Cl.$^3$ ............................................ A61K 31/53
[52] U.S. Cl. .................................................. 424/249
[58] Field of Search ......................................... 424/249

[56] References Cited

U.S. PATENT DOCUMENTS 3,966,728  6/1976  Murai et al. .......................... 424/249

Primary Examiner—Frederick E. Waddell
Attorney, Agent, or Firm—Jacobs & Jacobs

[57] ABSTRACT

A method of prevention and/or treatment of disorders of the liver, kidney, colon or rectum in mammals including humans which comprises administering to the patient a therapeutically effective amount of 2,4-diamino-6-(2',5-dichlorophenyl)-s-triazine maleate sufficient to prevent and/or overcome said disorders, and pharmaceutical compositions therefor.

5 Claims, 1 Drawing Figure

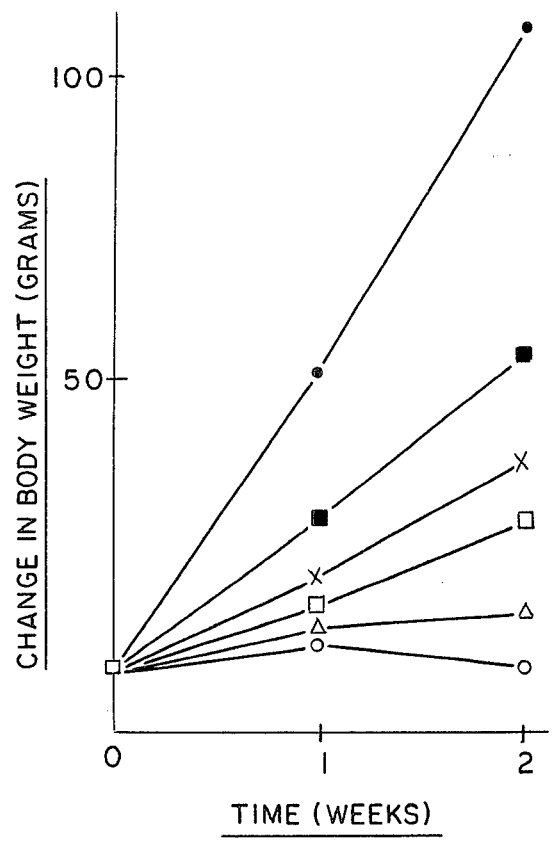
EFFECT OF THE PRESENT INVENTION
IN TREATING GUINEA PIGS SUFFERING
FROM COLITIS

TREATMENT OF DISEASES OF THE LIVER, KIDNEY, COLON AND RECTUM

The present invention relates to the use of 2,4-diamino-6-(2′, 5′-dichlorophenyl)-s-triazine maleate (hereinafter referred to as "compound I") in the treatment of disorders of hepatic cellular function, such as, for example, viral hepatitis, active chronic hepatitis, alcoholic hepatitis, hepatic diseases caused by pharmaceuticals or by toxins, hepatocirrhosis, and various other hepatic diseases, for treatment of disorders of renal cellular function such as, for example, glomerulonephritis, chronic nephritis, renal asteodystrophy, nephrotic syndrome, hemolytic uremic syndrome, arteriolosclerotic nephreosclerosis, etc. and for the treatment of diseases of the colon and rectum such as, for example, non-specific colitis, toxic colectasia, granulomatous colitis, ischemic procto-colitis, etc. The present invention also relates to pharmaceutical compositions containing compound I as the active agent.

Treatment of diseases of the liver, kidney, colon and rectum is primarily by way of diet or administration of nutritional supplements. Effective drugs for such diseases have been limited to, for example, adrenocortical hormones which have severe side effects. Therefore, there has been a long-felt need for the establishment of an effective treatment of these diseases using pharmaceuticals having a good therapeutic effect and improved safety.

The present invention is based on the discovery that compound I exhibits a cytoprotective action and is effective for treatment of hepatic and renal disorders and colitis. The effectiveness of compound I in experimental disease models in different organs and by different causes, is due to the protective action of compound I to cells that are fundamental constructive elements of the living body; this action is called a cytoprotective action.

The present invention includes a method of treatment of disorders of the liver, kidney, colon or rectum in mammals, including humans, which comprises administering to the sufferer an effective amount of compound I sufficient to overcome said disorders.

The present invention also includes a pharmaceutical composition for the treatment of disorders of the liver, kidney, colon or rectum in mammals including humans, which comprises an effective amount of compound I sufficient to overcome said disorders, in combination with a pharmaceutically acceptable carrier therefor.

Compound I may be administered as such or, preferably, as the pharmaceutical composition described above. The pharmaceutical compositions made administered orally, rectally or parenterally, and may be in the form of solid preparations, such as tablets, coated tablets, film tablets, hard or soft gelatin capsules, trouches, pills, granules, fine granules, powders, etc., semi-solid preparations, such as suppositories, and liquid preparations, such as injections, syrups, emulsions, suspensions, etc.

Examples of pharmaceutically acceptable carriers used in the manufacture of solid preparations are diluents (such as, for example, lactose, starch, mannitol, potassium hydrogen phosphate, etc.), binders (such as, for example, cellulose derivatives, polyvinyl alcohol, polyethylene glycol, gelatin, gum arabic, crystalline cellulose, etc.), disintegrating agents (such as, for example, carboxymethyl-cellulose, crystalline cellulose, low substituted hydroxypropyl cellulose, etc.), lubricants (such as, for example, magnesium stearate, talc, light silicic anhydride, synthetic aluminum silicate, etc.), coating agents (such as, for example, shellac, sucrose, precipitated calcium carbonate, talc, calcium hydrogen phosphate, etc.), plasticizers (such as, for example, castor oil, etc.) and polishing agents (such as, for example, carnauba wax, etc.).

Examples of carriers for semi-solid preparations are polyethylene glycol, various kinds of plant fats and hardened plant fats, (Witepsol® Dynamite-Nobel AG), etc. and surface active agents may be mixed with such carriers.

Liquid preparations can be manufactured by dissolving, emulsifiying or suspending compound I in, for example, distilled water, lower aliphatic alcohols (such as ethyl alcohol, etc.), glycol ethers (such as propylene glycol, etc.), fats and oils, etc. In that case, various kinds of surface active agents, gum arabic, gelatin, cellulose derivatives, etc. may be used as solubilizers, emulsifiers, suspending agents etc. as needed. Also isotonic agents (such as, for example, sodium chloride, etc.), preservatives (such as, for example, para-hydroxy benzoic acid derivatives or invert soaps) and buffers may be used.

All of the above-mentioned solid, semi-solid and liquid preparations may contain coloring agents, perfumes, flavoring agents, sweetening agents, or stabilizers therein. Further, such preparations may be made into long-acting preparations. It is also possible to make into microcapsules containing active ingredients.

The present invention preparations may also contain, besides compound I, other pharmaceuticals, such as, for example, digestive enzymes, antacids, gastric juice secreting inhibitors, aromatic stomach agents, bitter stomach agents, stomach mucous protective agents, anticholinic agents, etc. It is also possible to use compound I simultaneously with anti-inflammatory agents which may cause gastric disorder.

While oral administration of compound I is presently preferred, rectal or parental administration is often desirable.

The effective amount of compound I will depend, as is conventional, on a number of factors, such as the nature and severity of the disorder of the liver, kidney, colon or rectum, the weight of the sufferer, etc. Generally, the pharmaceutical composition will contain 0.05 to 99% of compound I. The daily dosage will generally be from 1 to 100 mg., but higher or lower dosages may be prescribed, as explained above. When a large amount is given, it is, of course, desirable to give unit doses several times a day by dividing the daily dose into smaller unit doses.

An example of tablets containing compound I is given below:

| | |
|---|---|
| Compound I | 5.0 mg/tablet |
| Corn Starch | 28.0 |
| Lactose | 73.4 |
| L-HPC | 13.0 |
| PVA | 4.0 |
| Magnesium stearate | 2.1 |
| Talc | 4.5 |
| | 130.0 mg |

Finely powdered compound (I) was mixed with starch, lactose, and L-HPC (low substituted hydroxypropyl cellulose) kneaded with an aqueous solution of PVA (polyvinyl alcohol) and made into granules for tablets by conventional methods. Then magnesium stearate and talc were added to the granules and tablets of suitable size were prepared.

Compound I is known per se see, e.g. U.S. Pat. No. 3,966,728. A typical synthesis is as follows. Thus, 44 grams of 2,5-dichlorobenzonitrile, 25.8 grams of dicyandiamide and 25 grams of sodium hydroxide were dissolved in 100 ml of methyl cellosolve and the solution was heated to reflux for five hours. After cooling, 500 ml of water was added thereto and separated crystals were collected by filtration. The crystals were recrystallized from dioxane to afford the desired product in the form of colorless crystals. Yield 58.5 grams. Melting point 268°–269° C. Analysis calculated for $C_9H_7N_5Cl_2$: C 42.21, H 2.76, N 27.35; Found: C 42.06, H 2.57, N 27.31.

The product obtained above was dissolved in dioxane, an equimolar amount of maleic acid was added thereto, and the mixture was evaporated to dryness under reduced pressure. The resulting residue was recrystallized from dioxane to afford the corresponding maleate, melting point 205° C. (with decomposition). Analysis calculated for $C_9H_7N_5Cl_2 \cdot C_4H_4O_4$: C 41.95, H 2.98, N 18.82; Found: C 42.15, H 2.86, N 18.72.

The present invention is illustrated by the drawing and the following Examples.

The drawing shows the effect of compound I when administered to guinea pigs having colitis caused by administration of amylopectine sulfate. These data show that administration of compound I greatly increases the body weight of the afflicted animals. The experimental procedure is set forth in Example 1.

EXAMPLE 1

Effect on colitis induced by administration of amylopectine sulfate (according to the method reported in J. Gastroenterology, 67, 473–483, 1974 by Marcus, R and Watt)

Sixty male guinea pigs of Hartley strain (body weight: 200 grams) were used. Among them, fifty guinea pigs were given tap water containing 1% amylopectine sulfate ("APS") as drinking water and were bred for four weeks. (APS contains about 15% sulfur.)

Two weeks after the administration of APS began, observations on body weight changes, diarrhea, and occult blood reaction in feces were made and the guinea pigs were divided into five groups (each group consisting of ten animals), each of which showed colitic symptoms. The animals in these five groups were administered 1 ml/kg/day of physiological saline solution and 5, 10, 25 and 50 mg/kg/day of compound I for two weeks by oral route. The other ten guinea pigs were untreated controls and were given untreated tap water as drinking water and were bred for four weeks under the same circumstances as those of the experimental groups.

After two weeks, the animals were killed by overinhalation of ether, the large intestines were removed and the degree of colitis was determined by observing the incidence of ulcers and the area of ulcers with a stereoscopic microscope ($\times 10$). The results are given in Table 1, and the changes in body weight during the administration of the compound I is given in the drawing.

TABLE 1

| Groups | Before Administration of the Compound I | | | | | After Administration of Compound I | | | |
|---|---|---|---|---|---|---|---|---|---|
| | Increase in Body Weight (0–2 Wks) | Nos of Symptoms Normal to Constipation | Diahhrea Soft Stool | Diahhrea Watery Stools | Nos of animals showing positive Occult Blood | Average Intake of APS (g/kg/2w) | Increase in Body Weight (2–4 wks) | Colitis Incidence | Symptom Area of Ulcer |
| Physiol. Saline Soln Compound I mg/kg/day | 51 ± 11 g | 1 | 7 | 2 | 9 | 0.85 | 2 ± 10 | 100% | 120 ± 24 mm² |
| 5 | 50 ± 12 | 1 | 7 | 2 | 8 | 0.91 | 11 ± 12 | 90 | 65 ± 20 |
| 10 | 48 ± 8 | 0 | 9 | 1 | 10 | 1.12 | 26 ± 15 | 80 | 50 ± 24 |
| 25 | 49 ± 9 | 1 | 7 | 2 | 9 | 1.26 | 36 ± 13* | 60 | 43 ± 15* |
| 50 | 49 ± 10 | 1 | 7 | 2 | 9 | 1.24 | 54 ± 10* | 60 | 34 ± 12* |
| Control Group | 106 ± 5 | 10 | 0 | 0 | 0 | — | 110 ± 11 | 0 | 0 |

*Significantly different from physiological saline solution group ($p < 0.05$)

Through the administration of compound I, improvement in the colitis followed by increase in body weight was observed. It is apparent that the resulting effect is not derived from a decrease of the cause for colitis because the intake of APS did not decrease, but rather increased. As a mechanism for the resulting colitis by administration of APS, the physico-chemical properties of APS must be involved. While the possibility of changes in bacteria in the intestines cannot be ignored, it has been determined that compound I does not exhibit any action on intestinal bacteria according to the standard test by Japan Antibiotic Association. Therefore, there is no contribution of antibacterial activity in the effect of compound I against colitis. In view of the above, it is clear that the effect of the compound I against colitis is due to the direct protection of large intestinal mucosal cells by compound I.

EXAMPLE 2

Effect on hepatic and renal disorders induced by administration of carbon tetrachloride Five groups of male rats of Sprague-Dawley strain (body weight: 200 grams) were used (ten rats per group). All of these rats were given 4 ml/kg of 50% carbon tetrachloride (used with olive oil) by oral route. After 24 hours, the rats were killed by decapitation, and blood was taken and the liver was isolated therefrom. Previously, the rats were fasted for 18 hours before taking blood therefrom. The blood was subjected to quantitative determination of GOT, GPT, LDH and BUN and the weights of isolated livers were measured.

Compound I was given to the rats of four groups, two to six hours after the administration of carbon tetrachloride (in other words, at the time when hepatic and renal disorders caused by carbon tetrachloride had already appeared) at the dose of 5, 10, 25 or 50 mg/kg by oral route. Physiological saline in an amount of 1 ml/kg/day to the rats of the fifth group. Rats of a sixth group that received no carbon tetrachloride, served as a control, and were also autospied, as above. The results are given in Table 2.

TABLE 2

| Groups | Dose (mg/kg) | Body Weight (g) | Liver Wt. (g) | GOT (Karmen Unit) |
|---|---|---|---|---|
| Physiol. Saline Solution | — | 198.7 ± 0.5 | 10.5 ± 1.9 | 3,91 ± 361 |
| Compound I | 5 | 198.6 ± 0.5 | 9.6 ± 2.2 | 2215 ± 250 |
|  | 10 | 199.1 ± 0.7 | 9.5 ± 2.5 | 1822 ± 249* |
|  | 25 | 200.6 ± 0.6 | 8.3 ± 1.5 | 15.1 ± 205* |
|  | 50 | 198.6 ± 0.8 | 7.4 ± 2.0 | 1339 ± 211* |
| Control (no C C/4) | — | 199.8 ± 0.6 | 5.9 ± 1.2 | 165 ± 20 |

| Groups | Dose (mg/kg) | GPT (Karmen Unit) | LDH (Wroblewski Unit) | BUN (mg/dl) |
|---|---|---|---|---|
| Physiol. Saline Solution | — | 2206 ± 298 | 22425 ± 9211 | 56.6 ± 10.6 |
| Compound I | 5 | 1920 ± 306 | 16341 ± 9009 | 42.0 ± 9.8 |
|  | 10 | 1566 ± 354 | 12209 ± 6214 | 34.6 ± 7.2 |
|  | 25 | 1012 ± 261* | 8054 ± 3666 | 31.4 ± 8.8 |
|  | 50 | 805 ± 134* | 5003 ± 1642* | 29.7 ± 3.5* |
| Control (no C C/4) | — | 38 ± 6 | 1864 ± 170 | 22.0 ± 1.8 |

*Significantly different from the groups given physiological saline solution by the t-test ($p < 0.05$)
Values show the average ± standard error of ten examples.

The data in Table 2 show that compound I depressed the increase of liver weight and the increase in GOT, GPT, and LDH, which are indices of hepatic disease. In addition, Compound I inhibited the increase of BUN which is an index of renal disorder. These results indicate that compound I exhibits an inhibitory action against hepatic and renal disorders. Since disorders in hepatic cellular function induced by carbon tetrachloride is an irreversible change, it will be apparent that the effectiveness of compound I is due to its cytoprotective action.

EXAMPLE 3

Enhancement of resistance of erythrocytic membrane

Sprague-Dawley strain rats were treated with heparine and blood samples were obtained therefrom. The blood was centrifuged at 3000 rpm for ten minutes to remove blood plasma and then washed with 10 mM phosphate buffer-physiological saline solution (pH 7) to wash erythrocyte. To each volume of blood required to obtain the erythrocyte, 19 volumes of hypoosmotic solution (containing 10 mM phosphate buffer) was added and an erythrocyte suspension (5% erythrocyte suspension) was prepared. With reference to hemolysis, the absorbancy (O.D.) at 540 nm using distilled water as the hypoosmotic solution so that completely hemolyzed was defined as "100% hemolysis".

An erythrocyte suspension with 0.4%/0.45% hypoosmotic saline solution was incubated at 37° C. for 30 minutes, centrifuged at 3000 rpm for 10 minutes, and the percent hemolysis was calculated from the O.D. of the supernatant liquid. Since compound I is hardly soluble in water (0.77 mM in saturated solution), 1 g of compound I was added to 100 ml of distilled water, the mixture was shaken for 30 minutes, centrifuged, and sodium chloride was added to the supernatant liquid to make the concentration of sodium chloride 0.4 and 0.45% whereupon the hypoosmotic solutions were prepared. The results are given in Table 3.

TABLE 3

|  | 0.4% Saline Solution | | 0.45% Saline Solution | |
|---|---|---|---|---|
|  | Percent Kemolysis Ratio | Inhibition Ratio | Percent Hemolysis Ratio | Inhibition Ratio |
| Control | 70.8 ± 0.6 | — | 27.5 ± 2.1 | — |
| Compound I 0.77 mM | 45.7 ± 1.8* | 35.5% | 10.4 ± 1.1* | 62.2% |

Percent hemolysis is an average of five experiments ± S.E.
*Significantly different from control. ($p < 0.05$)
It is clear that the compound (I) shows inhibition of hemolysis and exhibits protective action to erythrocyte membranes.

Example 4

Acute toxicity tests

The $LD_{50}$ values of compound I in ddY strain mice (6 weeks of age) and in Sprague-Dawley strain rats (7 weeks of age) are given in Table 4.

TABLE 4

| | | $LD_{50}$ Values (mg/kg) (95% fiducial limits) | | |
|---|---|---|---|---|
| | | Intraperitoneal Admn. | Subcutaneous Admn. | Oral Administration |
| Mice | Male | 775(419–977) | 2841(2529–3099) | 6035(5372–6962) |
|  | Female | 1006(886–1117) | 3216(2352–3551) | 5697(5057–6553) |
| Rats | Male | 802(776–834) | 1600(1424–1823) | 2898(2525–5108) |
|  | Female | 789(723–828) | 1524(1396–1668) | 2917(2479–3576) |

The $LD_{50}$ values of compound I are very large as compared with its effective dose for treatment of hepatic and renal disorders and colitis, and hence compound I may be regarded as highly safe.

The data in the present application demonstrate the cytoprotective effect of compound I against disorders of the liver, kidney, colon and rectum; compound I may thus be used for the prevention and/or treatment of disorders.

What is claimed is:

1. A method of treatment of disorders of hepatic cellular function in mammals including humans, which comprises administering to the patient a therapeutically effective cytoprotective amount of 2,4-diamino-6-(2′, 5′-dichlorophenyl)-s-triazine maleate sufficient to overcome said disorders.

2. The method according to claim 1, wherein said compound is administered to a patient suffering from viral hepatitis, active chronic hepatitis, alcoholic hepatitis, hepatocirrhosis or a hepatic disease caused by a pharmaceutical or a toxin.

3. The method according to claim 1, wherein said compound is administered to a patient suffering from hepatocirrhosis.

4. A method of treatment of disorders of hepatic cellular function induced by a toxin in mammals including humans, which comprises administering to the sufferer a therapeutically effective cytoprotective amount of 2,4-diamino-6-(2′, 5′-dichlorophenyl)-s-triazine maleate.

5. A method according to claim 1, wherein said disorder has been caused by a pharmaceutical or a toxin.

* * * * *